United States Patent [19]

Fenton, Jr. et al.

[11] Patent Number: 4,681,566

[45] Date of Patent: Jul. 21, 1987

[54] INFUSION DEVICE

[75] Inventors: Paul V. Fenton, Jr., Marblehead, Mass.; Robert L. Miller, New Providence, N.J.; Ernest M. Santin, Salem, Mass.

[73] Assignee: Strato Medical Corporation, Beverly, Mass.

[21] Appl. No.: 676,728

[22] Filed: Nov. 30, 1984

[51] Int. Cl.[4] .............................................. A61M 5/00
[52] U.S. Cl. ............................ 604/135; 128/DIG. 12
[58] Field of Search .................... 604/135, 30, 31, 38, 604/50, 65–67, 131, 134, 135, 151, 152, 154, 155, 245, 208; 128/DIG. 12, DIG. 13

[56] References Cited

U.S. PATENT DOCUMENTS

| | | |
|---|---|---|
| 3,279,653 | 10/1966 | Pfleger . |
| 3,886,938 | 6/1975 | Szabo et al. .......................... 604/135 |
| 4,085,747 | 4/1978 | Lee .............................. 128/DIG. 12 |
| 4,132,231 | 1/1979 | Puccio ................................. 604/131 |
| 4,136,802 | 1/1979 | Mascia et al. . |
| 4,202,333 | 5/1980 | Thill et al. . |
| 4,228,922 | 10/1980 | Takeshita . |
| 4,298,000 | 11/1981 | Thill et al. . |
| 4,333,459 | 6/1982 | Becker ................................ 604/135 |
| 4,381,006 | 4/1983 | Genese . |
| 4,430,079 | 2/1984 | Thill et al. . |
| 4,437,859 | 3/1984 | Whitehouse et al. ................ 604/131 |
| 4,470,317 | 9/1984 | Sabloewski et al. ................ 604/135 |
| 4,509,943 | 4/1985 | Hanzawa .................... 128/DIG. 13 |
| 4,565,500 | 1/1986 | Jeensalute ................... 128/DIG. 13 |
| 4,600,401 | 7/1986 | Kamen ........................ 128/DIG. 13 |

Primary Examiner—Stephen C. Pellegrino
Attorney, Agent, or Firm—Lahive & Cockfield

[57] ABSTRACT

An infusion device for a syringe having a tubular wall with a fluid dispensing opening at one end and an internal plunger. A device includes an element for driving the syringe plunger at a selected one of a set of predetermined spring-generated forces which are substantially constant over the range of motion of the plunger.

11 Claims, 13 Drawing Figures

INFUSION DEVICE

BACKGROUND OF THE DISCLOSURE

A present invention is in the field of medical instruments and more particularly is directed to a device for driving a fluid-dispensing syringe.

An infusion device is generally used to control the dispensing of fluids from a syringe, for example, to a capillary tube which in turn might introduce those fluids to a patient. In many cases, it is extremely important that the rate of fluid delivery be accurately controlled.

In the prior art, several types of infusion devices have been used. One type of device incorporates a housing for supporting a syringe and utilizes an electrical motor and associated drive circuitry configured to drive the plunger of the syringe at a constant rate. Typically such configurations incorporate a lead screw coupling between the electric motor and the plunger. Alternatively, direct gear couplers have been used. While these configurations are effective for driving a syringe plunger under certain circumstances, the dynamic range of the drive motor must be large enough to accomodate changes in flow resistance encountered at the fluid output port of the syringe. Typically, such resistance variations may be accommodated by maintaining sufficient driving capability in the circuitry and motor to offset the anticipated worst case flow resistance situation. One disadvantage of this configuration is the resulting size and weight of the infusion device which provides the necessary dynamic range.

Another form of prior art infusion device is exemplified by the configuration shown in U.S. Pat. No. 4,202,333. The device shown in that patent includes a spring-driven, constant force driver for a syringe plunger. In that configuration, a syringe is placed into an operating position within a supporting housing, which includes a pivoting actuating cover. When the pivoting actuating cover is closed, with the syringe in its operating position, a pre-loaded spring is coupled to the plunger in a manner automatically applying a constant force to the plunger. With this constant force driving the plunger, the fluid output rate from the syringe is variable, depending on the flow resistance encountered at the syringe output port. One particular advantage of this configuration is that there is no need for a relatively complex plunger driving motor and associated electrical circuitry. Consequently, such infusion devices may be made relatively small and lightweight, and may also be highly reliable. However, such devices in the prior art have been limited in their versatility, since each such device is limited to provide but a single constant force to a syringe plunger. Moreover, the prior art devices have not been adapted to monitor the output flow rate, measured as a function of the plunger movement.

It is an object that the present invention to provide an improved infusion device.

Another object is to provide an improved infusion device which may selectively apply one of a number of substantially constant forces to the plunger of a syringe.

Yet another object is to provide an improved infusion device which automatically applies a selected one of a plurality of predetermined constant forces to the plunger of a syringe.

Still another object is to provide an infusion device which monitors fluid flow from a syringe in response to spring driven plunger motion in a syringe.

SUMMARY OF THE INVENTION

The infusion device of the present invention is adapted for coupling to a syringe having an elongated tubular wall extending along a tube axis and a fluid dispensing opening at one end. The syringe includes an internal plunger which may be moved along the tube axis to drive fluid out of the fluid dispensing opening from the region within the tubular wall. The infusion device includes an assembly for driving the plunger over a predetermined range of motion along the tube axis at a selected one of a set of at least two substantially constant, spring-operated forces. A plunger driver is operative when the syringe is coupled to the device in an operating position, and is inoperative otherwise.

More particularly, in one form, the spring driver includes first and second springs, and an actuator which is selectively operable in one state to couple one of the springs to the plunger and in a second state to couple both of the springs to the plunger. A controller controls the actuator to be in a selected one of those driving states when the syringe is coupled to the device and the operating position. In other forms of the invention, additional springs might also be used and the actuator may couple one or more of those springs to the plunger in various combinations to apply one of a plurality of a set of substantially constant forces to the plunger.

In one form of the invention, the automatic selection of the particular force applied to the plunger may be accomplished by a sub-assembly of the actuator which is responsive to interaction with the syringe itself in the operating position, so that the selected state (i.e. force applied to the plunger) is related to the geometry of the syringe. With this configuration, for example, one size syringe in the infusion device may result in a first force applied to the plunger, and second size syringe may result in a second force applied to the plunger, with suitable calibration of these forces to desired fluid delivery requirements. For example, with the particular geometries of two different sized syringes, the pressures at the flow dispensing ports in both cases might be the same.

In alternative configurations, the controller may be operable to control the state of the actuator in response operator-applied force. For example, the operator may manually cause a particular combination of springs to be coupled to the plunger.

In one particular form of the invention, the infusion device includes a housing having a base member and an elongated cover member. In this form, the base member includes a pair of the elongated cavities extending from one surface and to the interior of that member. Each of those cavities extends along an associated one of the pair of parallel cavity axes. The actuating cover member is pivotably coupled at one end to the base member, permitting a predetermined range of angular motion of that cover member with respect to the base member about a cover axis perpendicular to the cavity axes. The cover member is positionable in a first position minimally angularly offset about the cover axis and in a second position maximally angularly offset about the cover axis.

The housing includes a syringe positioning assembly for supporting the syringe in the first cavity in an operating position with the plunger extended from its minimum position and ready for depression to dispense fluid. The syringe positioning assembly further is adapted to couple the fluid dispensing opening of the syringe through the housing along an axis substantially parallel to the first cavity axis. In various forms of the invention, particular fittings may be used to accommodate selected syringe geometries so that many forms of conventional-type syringes may be used with the infusion device.

The plunger driving assembly includes a driving member positioned in the first cavity and adapted for linear motion along the first cavity axis. A spring carrier member is positioned in the second cavity and is adapted for linear motion along the second cavity axis. A sliding coupler assembly is provided to couple the spring carrier member to the plunger driving member.

A first leaf spring has one end affixed to, and is wound about, an elongated spring support mounted to the carrier member and extending along an axis perpendicular to the second cavity axis. A second leaf spring has one end affixed to, and is wound about, a spring support mounted to the spring carrier member and extending along an axis perpendicular to the second cavity axis.

First and second spring puller members are also positioned within the second cavity and adapted for linear motion along the second cavity axis. The second end of the first leaf spring is affixed to the first spring puller member, and the second end of the second leaf spring is affixed to the second spring puller member, with the second spring puller member being positioned between the spring carrier member and the first spring puller member.

The actuating cover member is coupled at a point displaced from the cover axis to the first spring puller member by a predetermined length link member. The link member is pivotably coupled at one end to the actuating cover member and is pivotably coupled at its other end to the first spring puller member. With this configuration, when the actuating cover member is in its first (or closed) position, i.e., the actuating position, where it is minimally displaced from the cavity axis, the first spring puller member is position along the second cavity axis at a point in its range of motion farthest from the cover axis. When the actuating cover member is in its second (or open) position, the first spring puller member is positioned along the second cavity axis at a point in its range of motion nearest to the cover axis.

With this configuration, when the cover is opened, the plunger drive member is displaced maximally from the fluid exit of the housing, permitting insertion of a syringe into the first cavity. When the actuating cover member is positioned to its second (or closed) position, the plunger driver is automatically biased with a constant spring-generated force against the plunger. Accordingly, an interlock is provided where the force is only applied to the plunger of the syringe when the cover member is in its actuating, or closed, position.

A drive coupler is selectively positionable in a first drive position to couple the first spring puller member to the second spring puller member. In this position, the first and second springs together drive the plunger of the syringe. The drive coupler is also selectively positionable in a second drive position where the spring puller members are decoupled. In this position, only the first spring drives the plunger of the syringe. A selectively operable controller controls the drive coupler to be in a selected one of the first and second drive positions when the syringe is coupled to the infusion device in its operating position.

In one form of the invention, the drive cuppler may be automatically controlled to its position by means of an interaction with the syringe so that the selected state is related to the geometry of this syringe. Alternatively, an operator-applied force may be used to select the position of the drive coupler.

In any of the forms of the invention, a selectively operable flow detector may monitor fluid flow through the fluid dispensing opening of the syringe. The flow detector includes a sensor for generating a motion signal representative of movement of the plunger along the tube axis within its range of motion. An alarm is responsive to the motion signal to generate an alarm signal when the motion signal is representative of plunger movement along the tube axis at a rate outside a predetermined range. The flow detector in some forms of the invention may be operable only when the syringe is in the operating position. In addition, the flow detector may also be operative only when a plunger is in its operating range ofmotion and not at the end of that range.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figures 1, 2:
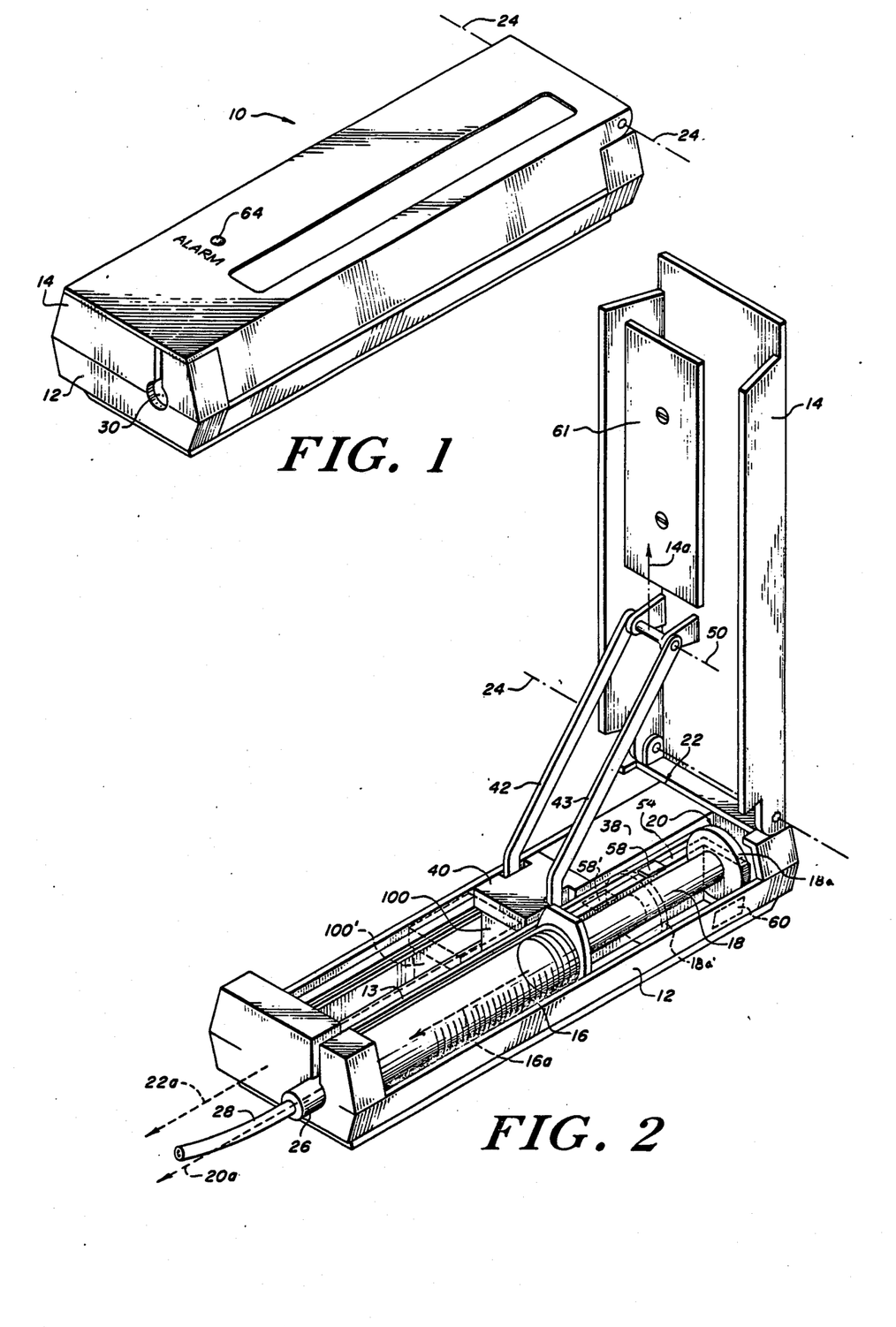
FIGS. 1 and 2 show perspective views of an exemplary embodiment of an infusion device in accordance with the present invention.
Figure 3:
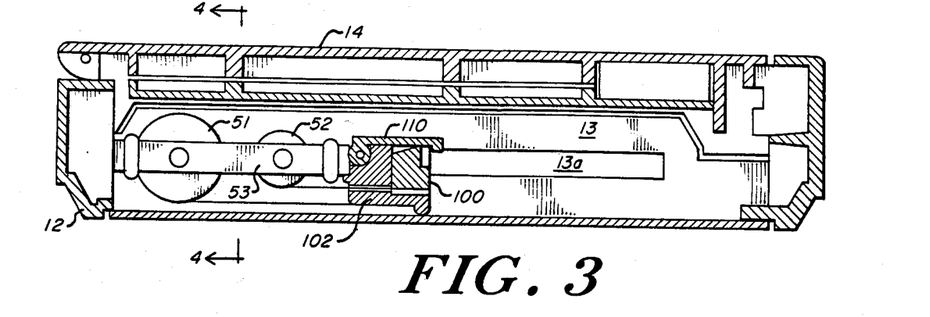
FIG. 3 shows a sectional view of the infusion device of FIGS. 1 and 2 along the second cavity axis.
Figure 4:
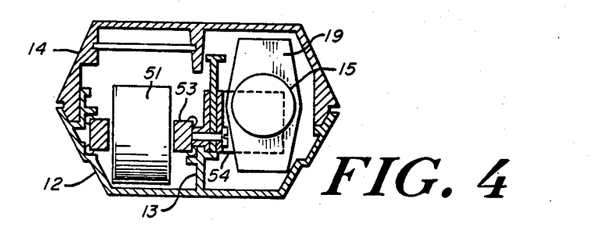
FIG. 4 shows a sectional view of the infusion device of FIG. 3 along the lines 4—4.

FIGS. 1 and 2 generally show an infusion device 10 in a perspective view. Device 10 includes a housing having a base member 12 and an actuating cover member 14. The device 10 is adapted for use with a syringe. FIG. 2 shows the device 10 with its cover member open and an exemplary syringe in the operating position. The syringe has a tubular wall portion 16 extending along a tube axis 16a with a fluid dispensing opening (not shown in FIG. 2) at one end, and a plunger 18 adapted for motion along the tube axis 16a in response to forces applied to the plunger 18. The plunger 18 includes a pusher member 18a.

The base member 12 includes a pair of elongated cavities 20 and 22 seperated by an inter-cavity wall 13. The cavities 20 and 22 extend along associated ones of a pair of parallel cavity axes 20a and 22a. The actuating cover member 14 is elongated and extends along a cover member axis 14a. The actuating cover member 14 is pivotably coupled to the base member 12 permitting a range of angular motion of the cover member 14 with respect to the base member 12 about a cover axis 24 (which is perpendicular to the cavity axes).

The syringe is adapted to be fitted with an end adaptor 26 having a capillary tube 28 extending therefrom. The base member 12 includes a slot and hole portion 30 which is adapted to permit the insertion of the syringe with its adaptor 26 and tube 28 through the slot and hole portion 30 so that the syringe may be positioned within the cavity 20. A syringe positioning member 32 (not shown in FIG. 2) supports the shoulder 19 of the tubular portion of the syringe within the cavity 20 so that the syringe is in the operating position as shown in FIG. 2. In the operating position, the tube axis 16a is substantially parallel to the cavity axes. In the operating position, the plunger 18 maintains a dynamic range along the tube axis 16a between tube predetermined reference points.

The plunger driving assembly includes a plunger drive member 54 in the first cavity 20 and associated assemblies in the second cavity 22. The 3-6 below, and generally include a pair of wound leaf. springs 51 and 52 on a spring carrier member 53 (indicated generally in FIG. 2 by reference designation 38), a pair of selectively coupled spring puller members 100 and 102 (indicated generally by reference designation 40), and two link members 42 and 43. The link members couple one of the spring puller members with the actuating cover member 14. The link members are pivotably coupled to the actuating cover member 14 about an axis 50 which is parallel to the cover axis 24, and those link members are pivotably coupled to one of the spring puller members about an axis parallel to the cover axis 24. The spring puller members 40 and the spring carrier member 53 are all adapted for linear motion in the direction of the second cavity axis 22a.

With this configuration, the cover member is positionable between first and second cover positions, with the first (or open) cover position being shown in FIG. 2 where the cover member 14 is maximally angularly displaced with respect to the cavity axes, and the second (or closed) cover position shown in FIG. 1 where the cover member 14 is minimally angularly displaced with respect to the cavity axes.

As will be described in detail below, when the cover member 14 is in its first cover position, the plunger driving member 54 is maximally displaced from the opening 30 in base member 12, as are the pair of spring puller members 40. In this position, a syringe may be inserted into the cavity 20 to be in the operating position. Thereafter, when the cover member 14 is shifted to its second cover position, at least the first spring puller member of the pair 40 is displaced to its position closest to the hole 30 of base member 12 in a matter applying a substantially constant spring-generated force to the plunger driving member 54, which in turn applies this force to the plunger 18 of the syringe. In response to this force, the plunger driving member 18 is driven along the tube axis with a substantially constant force, with the rate of motion being determined by the flow resistance encountered by the fluid exiting from the region interior to the tubular wall 16 and through the tube 28.

A plunger position sensor is indicated generally within cavity 20 by the dotted rectangle denoted by reference designation 60. In one form of the invention, the sensor 60 may be a conventional optical detector for detecting motion of the plunger 18 using a "bar-code" type sensing arrangement. Alternatively, an electro-mechanical arrangement may be used where a series of switches is actuated by the motion of the plunger 18.

Figure 10:
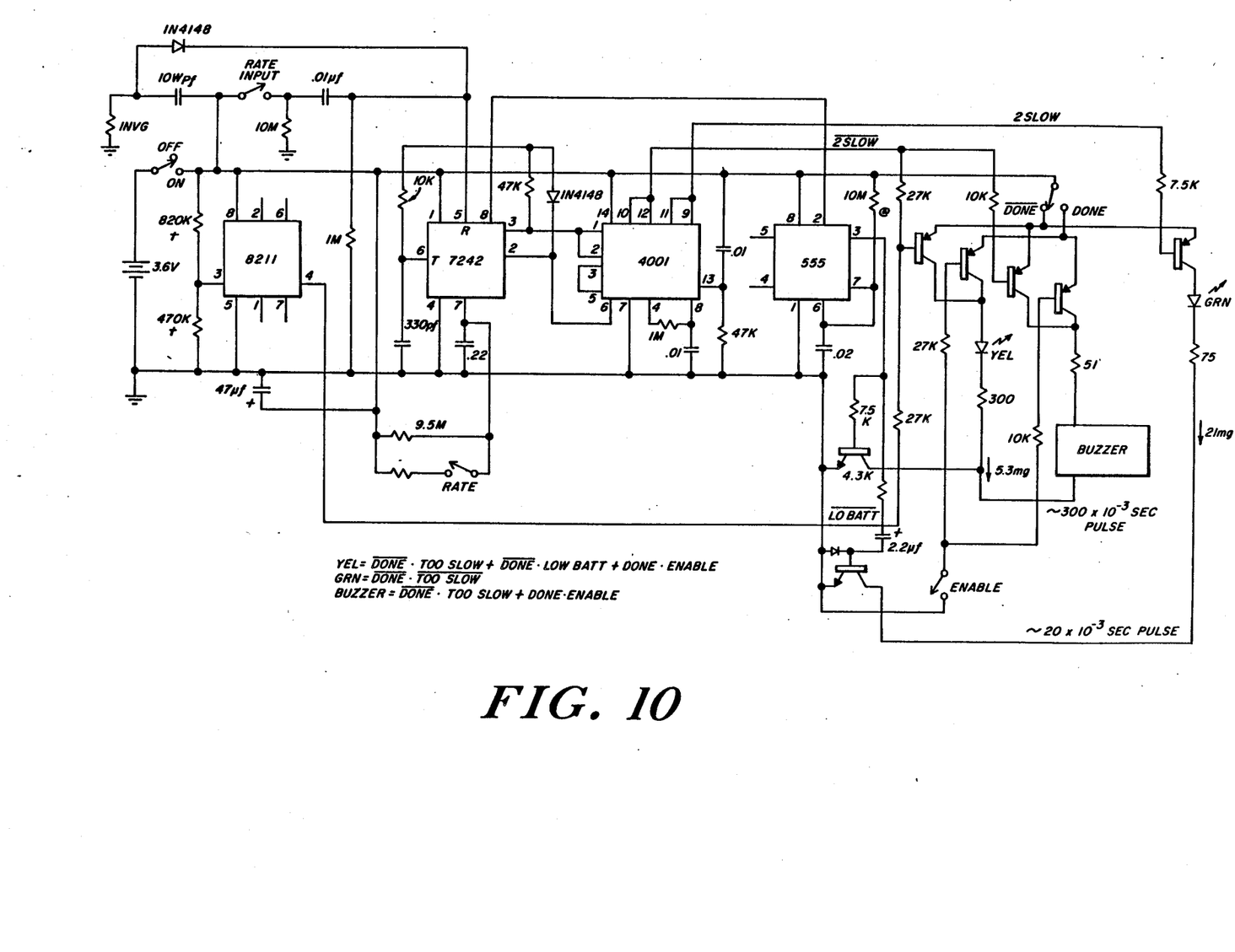
FIG. 10 is an electric schematic diagram for an exemplary fluid flow monitoring circuit for the infusion device of FIGS. 1 and 2.

An alarm circuit may be provided, as indicated by element 61, which is responsive to the signal generated by sensor 60 to provide a visual signal with an indicator 64 when the motion of plunger 18 is at a rate outside a predetermined range. In the present embodiment, an exemplary monitoring and alarm circuit is used in the form illustrated schematically in FIG. 10 providing both visual and audible alarms.

Figure 5:
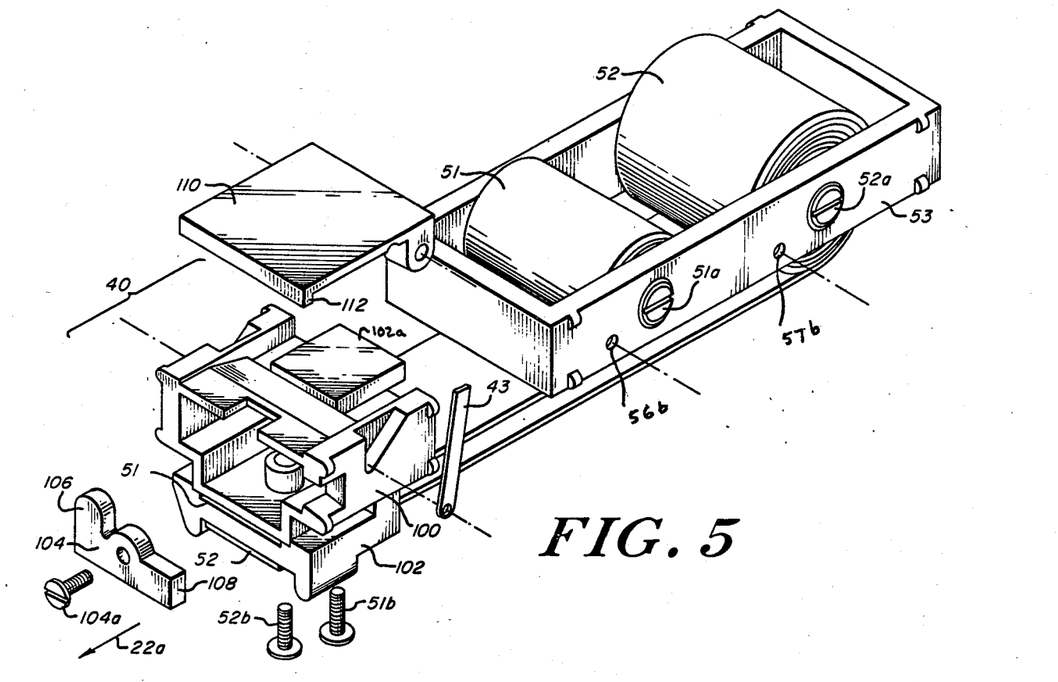
FIGS. 5 and 6 show exploded perspective views of the plunger drive assembly of the infusion device of FIGS. 1 and 2.

FIGS. 5, 6 and 6A-6C illustrate certain of the operative elements in the infusion device 10 in exploded, perspective form. FIG. 5 shows a first and second coiled leaf springs 51 and 52, respectively mounted to a spring carrier member 53 adapted for linear motion along axis 22a. Springs 51 and 52 each have a first end affixed to an elongated spring support fixed to the spring carrier member 53. There support spring supports 51a and 52a extend along axes perpendicular to the second cavity axis 22a. The other ends of the respective springs 51 and 52 extend along the second cavity axis 22a, and are coupled to respective ones of the spring puller members of pair 40, as described below. The spring carrier member 53 is rigidly coupled to the "L-shaped" spring driver member 54 which is positioned within the first cavity 20. By way of example, that coupling may take the form of shoulder screws 56 and 57 (shown in FIG. 6) which pass through an elongated opening 13a in the inter-cavity wall 13 in base member 12.

The pair of spring puller members 40 are and also shown in FIG. 5. These puller members include a first spring puller member 100 and a second spring puller member 102. Each of members 100 and 102 are adapted for linear a motion along the second cavity axis 22a. The second end of the leaf spring 51 is coupled to the underside of the first puller member 100 by a screw fastener 51b. Similarly, the second end of spring 52 is coupled to the underside of puller member 102 by a screw fastener 52b.

The first puller member 100 includes a rocker member 104 which is adapted by screw 104a for pivotal motion about an axis parallel to the cavity axis 22a. The rocker member 104 includes a pusher portion 106 at one end and an input portion 108 at the other end. The input portion 108 extends beyond the members 100 and 102 through the opening 13a (shown in FIG. 3) and is adapted for pivotal motion in response to forces applied by an actuating ramp portion 55a of the plunger driver member 54, described below.

The puller member 102 includes a drive coupler member 110 affixed to a portion 102a thereof. Drive coupler member 110 includes a hinged coupling portion 112 at its forward end. The coupling portion 112 includes a lip underlying its forward end which is adapted for selective engagement with the forward portion of the member 100 in one position, and is adapted to decouple, or disengage, that forward portion of the pulling member 100 when the coupling portion 112 is displaced vertically from its nominal position engaging member 100 shown in FIGS. 3, 7 and 9. In operation, the rocker member 104 controls the position of coupler portion 112 of the drive coupler 110 in response to actuator forces applied by the ramp portion 55a of the drive member 54.

Figure 6:
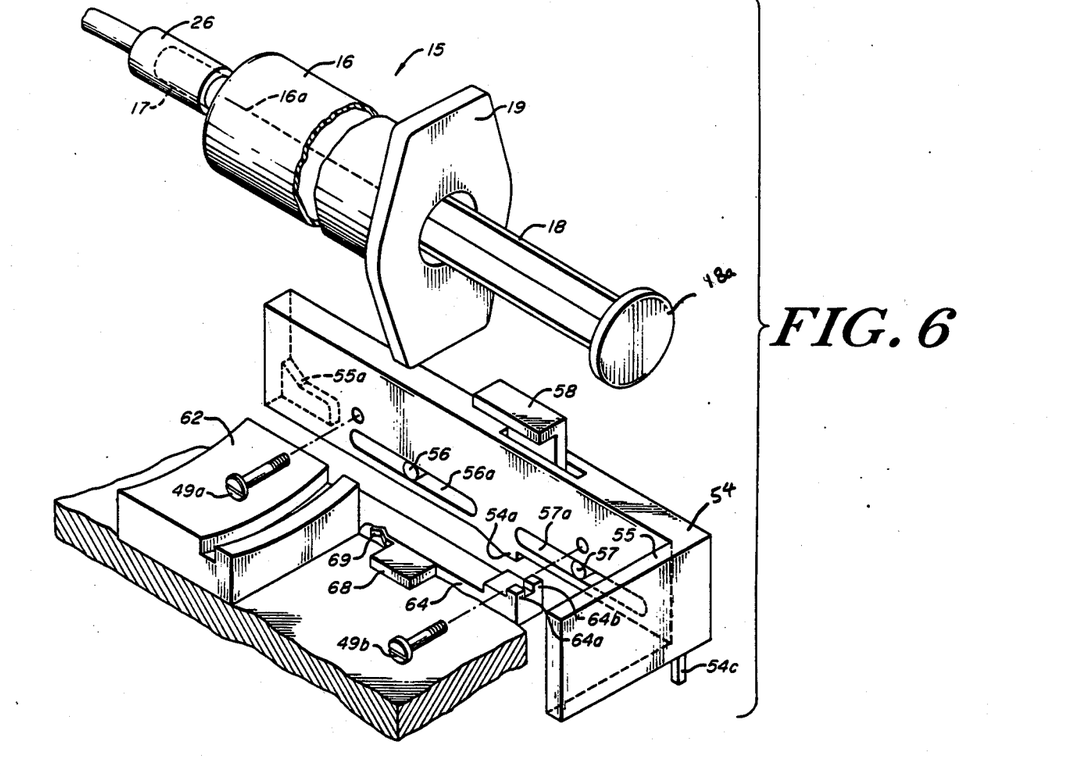

FIG. 6 shows the syringe support assembly and plunger drive member in detail. The syringe positioning member 62 is shown, with a slot to accommodate the shoulder 19 of the syringe 15 so that the syringe is in the operating position with the element 26 passing through the hole 30 of the housing. The positioning member 62 includes a hinged lever member 64 extending in the direction of the first cavity axis 20a and including stop members 64a and 64b at its tip. Member 64 includes a flexure portion (not shown) which permits the distal tip of that member 64 to be displaced about an axis perpendicular to the cavity axis 20a. An "end-of-excursion" switch 68 with an actuating arm 69 is affixed to the base of cavity 20 for detecting the maximum excursion of the plunger 18. In the illustrated embodiment, the device 10 is adaptable for various size syringes through the manual application by an operator of a force to a selector member 58.

The end portion 55 of the L-shaped plunger driver member 54 is adapted for driving the pusher 18a of the plunger 18 of the syringe 15. The plunger driver member 54 is adapted for substantial linear motion along the direction of axis 20a and is constrained to such motion by the shoulder screws 56 and 57 pass through slots 56a and 57a respectively of member 54, the opening 13a of wall 13, and into receiving holes 56b and 57b of member 53. The plunger driver member 54 includes on its lower surface a pair of plunger stop members 54a and 54b and an "end-of-excursion" arm member 54c extending downward from the end portion 55. Member 54 further includes an actuating ramp portion 55a.

A selector member 58 of member 54 is pivotally coupled to member 54 and positioned substantially within an interior void region (or cavity) 54' of member 54. This portion of member 54 is shown in detail in FIGS. 6A-6B. Selector member 58 includes a pair of spring arms 58a and 58b, a release portion 59a and an actuating portion 59b. The selector member 58 is maintained by spring portions 58a and 58b to be nominally in the position as shown in FIG. 6A, that is with release portion 59a adjacent to pin 57 and actuating portion 59b adjacent to lever arm 64.

Figure 6A:
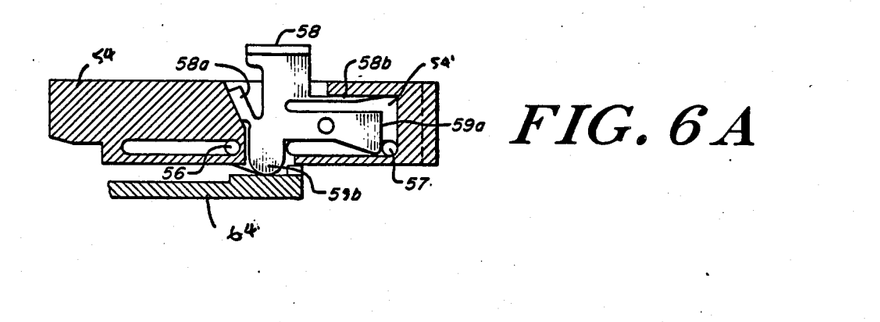
FIGS. 6A, 6B and 6C show sectional views of a portion of the plunger driver of the infusion device of FIGS. 1 and 2.
Figure 6B:
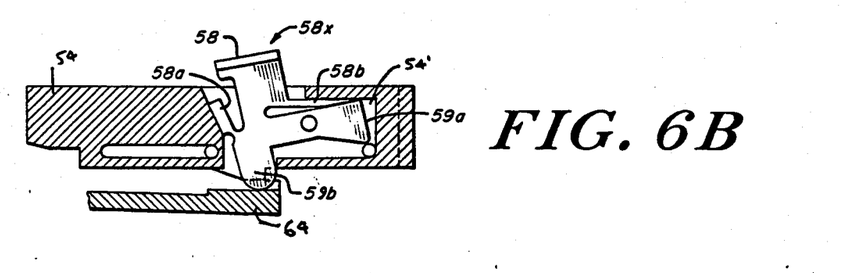
Figures 6C, 7:
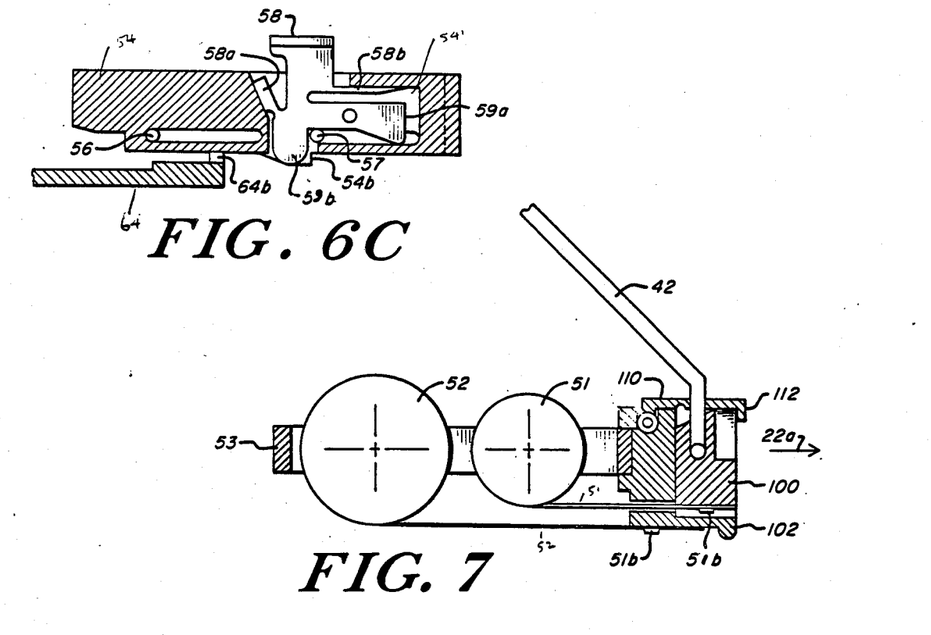
FIGS. 7-9 are schematic representations of portions of the infusion device of FIGS. 1 and 2, illustrating the operation of that device.
Figures 8, 9:
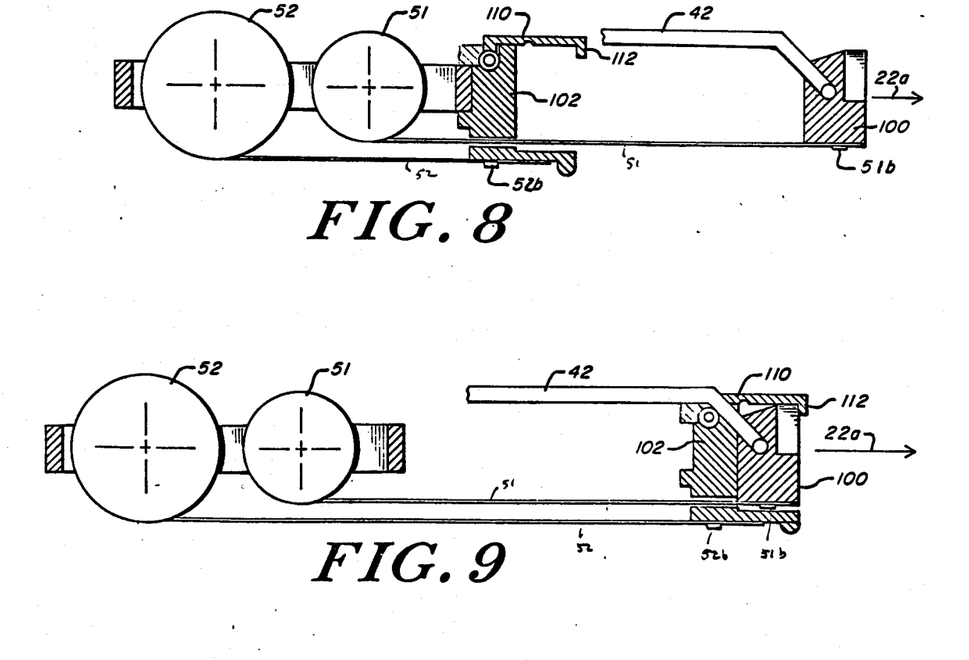

With the cover member 14 in its open position, member 58 may be positioned as illustated in FIG. 6A and the infusion device 10 is in a nominal position for receiving a small (for example, 10 cc) syringe and for coupling just the spring force provided by spring 51 to the plunger 18 of that syringe by way of puller member 100 and plunger drive member 54. In FIG. 7, the puller member 100 is shown at its point in its range of motion nearest to the cover axis 24. In this nominal position, occurring when the selector member 58 is biased rotatably "back" (as shown in FIG. 6A) within the cavity in member 54, the release portion 59a of member 58 is interferingly engaged with screw 57 and the actuating portion of that selector member 58 is resting on the top surface of member 64, permitting the portions 54a and 54b of member 54 to be interferingly engaged with the corresponding stop members 64a and 64b of the member 64. With the member 54 is this position, the ramp 55a is positioned in a manner displacing the input portion 108 of rocker member 54 so that the pusher portion 106 of that rocker 104 displaces the end 112 of drive coupler 110 so that the puller. members 100 and 102 are decoupled. As a result, when the syringe 15 is positioned within cavity 20 in the operating position, and the cover member 14 is closed, the puller member 100 is driven forward to accommodate the full extension of plunger member 18 in the cavity 20a and the force from spring 51 is applied to the plunger. As the plunger traverses along the axis 16a (in the operating position, with tube axes 16a parallel to cavity axis 20a, and the shoulder member 19 positioned within the syringe support member 62), the portion 55 of drive member 54 drives the plunger 18 along axis 16a until it reaches the full extent of its motion where the extension member 54c engages with the arm 69 of switch 68 indicating the end of operation. In some embodiments, this may be coupled to an audible alarm, for example, to alert a user that the syringe is fully emptied. The initial starting point, after the cover member is closed, of this configuration is shown in FIG. 8 with the first spring puller member 100 positioned at the point in its range of motion farthest from its cover axis 24.

In order to accommodate a larger syringe, with a driving force provided by both springs 51 and 52, the cover member 14 may be positioned to its open position, with the drive member 100 at its point in its range of motion nearest to the cover axis 24, as shown in FIG. 7. Then, to insert the larger syringe, the selector member 58 may be pivoted in the direction of reference arrow 58x (counter clockwise as shown in FIG. 6B) with the result that the actuating portion 59b depresses the end portion of lever 64 so that the stop members 54a and 54b of member 54 are no longer engaged with the stop members 64a and 64b of lever arm 64 and further so that the release portion 59a of selector member 58 is raised above the screw 57. Then, the plunger drive member 54 may be positioned by the operator farther back in the cavity (that is, toward cover axis 24) in order to accommodate the larger (for example, 20 cc) syringe with the new starting position of plunger 18 and the selector member 58 positioned as shown in FIG. 6C. Since the plunger drive member 54 has been positioned back in cavity 20 toward cover axis 24, the actuating ramp portion 55a of drive member 54 releases the rocker 104 so that the pusher portion 106 is pushed down and the coupler portion 112 of drive coupler 110 engages the forward edge of the puller member 100, thereby coupling the spring puller members 100 and 102, as shown in FIG. 9. Thereafter, the cover member 14 may be positioned to its closed position as shown in FIG. 9. In this position, operation of the infusion device 10 is similar to that described above, except that the combined spring force produced by both of springs 51 and 52 drives the plunger 18 along axis 16a. In alternative embodiments, the selector member 58 may be replaced by an element in the cover member 14 which is specifically adapted for the differences in geometry of the two or more different size syringes to be used with the device 10 so that based on one geometry, the drive coupler is one position and based on another geometry, the drive position is in its other position.

Thus, with this operation, a syringe may be positioned within the infusion device 10, and driven with a selectable one of two driving forces which are substantially constant over the range of motion of the plunger of the syringe. The drive forces may be in one case that provided by a first leaf spring and in another case by the sum of the forces provided by two leaf springs. The device is safely operable by personnel in a fail-safe mode in that the appropriate spring force is automatically determined by the geometry of the device and moreover, that the infusion is operatively performed only when a syringe is in the appropriate operating position. Furthermore, the associated electronic circuitry and sensors provides the alarm signals when the syringe infusion operation is complete and also when the rate of plunger motion, or delivery of fluid from the syringe, is outside a predetermined range. Moreover, the resultant system is lightweight and requires no external power supply for the plunger driving assembly, although relatively small and lightweight battery assemblies may typically be used to drive the electronics associated with the sensor and alarm circuitry.

The invention may be embodied in other specific forms without departing from the spirit or essential characteristics thereof. The present embodiments are therefore to be considered in all respects as illustrated and not restrictive, the scope of the invention being indicated by the appended claims rather than by the foregoing description, and all changes which come within the meaning and range of equivalency of the claims are therefore intended to be embraced therein.

We claim:

1. An infusion device adapted for coupling to a syringe having an elongated tubular wall extending along a tube axis with a fluid dispensing opening at one end and having an internal plunger adapted for motion along said tube axis, said device comprising spring driving means for driving said plunger over a predetermined range of motion along said tube axis in response to an applied force, means for generating at least two substantially constant, spring generated forces, means for selectively coupling said force generating means, including means for generating said applied force and for applying said applied force to said spring driving means by selectively coupling one or more of said spring-generated forces to said spring driving means, said spring-driving means being operative when said syringe is coupled to said device in an operating position, and being inoperative otherwise.

2. An infusion device according to claim 1 wherein said spring-driving means includes:
   A. a first spring and a second spring,
   B. a multi-state actuator selectively operable in a plurality of states, said actuator being coupled to said first spring in a first actuator state and operable in said first actuator state to apply a first one of said spring-generated forces to said plunger, and said actuator being coupled to said second spring in a second actuator state and operable in said second actuator to apply a second one of said spring-generated forces to said plunger, and
   C. control means for controlling said actuator to be in a selected one of said states when said syringe is coupled to said device in said operating position.

3. An infusion device according to claim 2 wherein said control means is operable to control the state of said actuator in response to an operator-applied force.

4. An infusion device according to claim 2 further comprising:
   selectively operable flow detector means for monitoring fluid flow through said opening, including sensor means for generating a motion signal representative of the movement of said plunger along said tube axis within said range of motion, said sensor means being operative when said syringe is in said operating position, and
   alarm means responsive to said motion signal to generate an alarm signal when said motion signal is representative of plunger movement along said tube axis at a rate outside a predetermined range.

5. An infusion device according to claim 4 further comprising an alarm controller means for controlling said flow detector means to be operative when said syringe is in said operating position and to be inoperative otherwise.

6. An infusion device according to claim 1 further comprising:
   selectively operable flow detector means for monitoring fluid flow through said opening, including sensor means for generating a motion signal representative of the movement of said plunger along said tube axis within said range of motion, said sensor means being operative when said syringe is in said operating position, and
   alarm means responsive to said motion signal to generate an alarm signal when said motion signal is representative of plunger movement along said tube axis at a rate outside a predetermined range.

7. An infusion device according to claim 6 further comprising an alarm controller means for controlling said flow detector means to be operative when said syringe is in said operating position and to be inoperative otherwise.

8. An infusion device adapted for coupling to a syringe having a tubular wall extending along a tube axis with a fluid dispensing opening at one end and having an internal plunger adapted for motion along said tube axis, and including means for spring-driving said plunger over a predetermined range of motion along said tube axis at a selected one of a set of at least two substantially constant, spring-generated forces, said spring-driving means being operative when said syringe is coupled to said device in an operating position, and being inoperative otherwise, said device comprising:
   A. a housing having a base member and an elongated actuating cover member extending along an actuating cover member axis, said base member including a pair of elongated cavities extending from one surface of and into the interior of said base member, each of said cavities extending along an associated one of a pair of parallel cavity axes, said actuating cover member being pivotably coupled at one end to said base member to permit a predetermined range of angular motion of said actuating cover member with respect to said base member about a cover axis perpendicular to said cavity axes, said actuating cover member being positionable in a first cover position whereby said actuating cover member is minimally angularly offset about said cover axis with respect to said cavity axes, and being positionable in a second cover position whereby said actuating cover member is maximally angularly offset about said cover axis with respect to said cavity axes,
   B. syringe positioning member affixed to said housing, said syringe positioning member including means for positioning said syringe within said first cavity in said operating position with said plunger being positioned within said tubular wall at a point along said tube axis spaced apart from said outlet and with said tube axis being substantially parallel to said first cavity axis, and including means for coupling said opening through said housing along an axis substantially parallel to said first cavity axis,
   C. a plunger driving assembly including:

i. a plunger driving member positioned within said first cavity and adapted for linear motion along said first cavity axis,
 ii. a spring carrier member positioned within said second cavity and adapted for linear motion along said second cavity axis,
 iii. means for coupling said spring carrier member to said plunger driving member,
 iv. a first leaf spring being affixed at its first end to an elongated spring support affixed to said spring carrier member and extending perpendicular to said second cavity axis,
 v. a second leaf spring being affixed at its first end to an elongated spring support affixed to said spring carrier member and extending perpendicular to said second cavity axis,
 vi. a first spring puller member positioned within said second cavity and being adapted for linear motion between two predetermined first puller reference points along said second cavity axis,
 vii. a second spring puller member positioned within said second cavity and being adapted for linear motion between two second puller reference points along said second cavity axis, said second puller member being positioned between said spring carrier member and said first spring puller member,
 viii. means for fixedly coupling the second end of said first leaf spring to said first spring puller member,
 ix. means for fixedly coupling the second end of said second leaf spring to said second spring puller member,
 x. means for coupling said actuating cover member at a point displaced from said cover axis to said first spring puller by a predetermined length link member, said link member being pivotably coupled at one end to said actuating cover member about an axis perpendicular to said second cavity axis, and being pivotably coupled at its other end to said first spring puller member about an axis perpendicular to said second cavity axis, whereby said first spring puller member is positioned along said second cavity axis at a point in its range of motion nearest to said cover axis when said actuating cover member is in its second cover position, and at a point in its range of motion farthest from said cover axis when said actuating cover member is in said first cover position,
 xi. drive coupler selectively positionable in a first drive position to couple said first spring puller member to said second spring puller member, and selectively positionable in a second drive position to decouple said first spring puller member from said second spring puller member,
 xii. selectively operable control means for controlling said drive coupler to be in a selected one of said first and second drive positions when said syringe is coupled to said device in said operating position.

9. An infusion device according to claim 8 wherein said control means is operable to control the position of said drive coupler in response to an operator-applied force.

10. An infusion device according to claim 8 further comprising:
 selectively operable flow detector means for monitoring fluid flow through said opening, including sensor means for generating a motion signal representative of the movement of said plunger along said tube axis within said range of motion, said sensor means being operative when said syringe is in said operating position, and alarm means responsive to said motion signal to generate an alarm signal when said motion signal is representative of plunger movement along said tube axis at a rate outside a predetermined range.

11. An infusion device according to claim 10 further comprising an alarm controller means for controlling said flow detector means to be operative when said syringe is in said operating position and to be inoperative otherwise.

* * * * *

UNITED STATES PATENT AND TRADEMARK OFFICE
CERTIFICATE OF CORRECTION

PATENT NO. : 4,681,566

DATED : July 21, 1987

INVENTOR(S) : Paul V. Fenton, Jr., Robert L. Miller and Ernest M. Santin

It is certified that error appears in the above-identified patent and that said Letters Patent is hereby corrected as shown below:

Column 2, line 16: "spring-operated" should read --spring generated--.

Column 2, line 53: "elongated cover" should read --elongated actuating cover--.

Column 4, line 22: "ofmotion" should read --of motion--.

Column 5, lines 24 and 25: "The 3-6 below, and generally include a pair of wound leaf. springs 51 and 52" should read --The latter sub-assemblies are shown in detail in Figs. 3-6 below, and generally include a pair of wound leaf springs 51 and 52--.

Column 7, line 5: "shown, with" should read --shown with--.

Column 7, line 43: "actuatinq" should read --actuating--.

Column 7, line 66: "puller.members" should read --puller members--.

Column 8, line 27: "actuating portion 59b" should read --actuating portion 57b--.

Column 9, line 24: "witha" should read --with a--.

UNITED STATES PATENT AND TRADEMARK OFFICE
CERTIFICATE OF CORRECTION

PATENT NO. : 4,681,566
DATED : July 21, 1987
INVENTOR(S) : Paul V. Fenton, Jr. et al It is certified that error appears in the above-identified patent and that said Letters Patent is hereby corrected as shown below:

Column 9, line 50: "actuator to" should read --actuator state to--.

Signed and Sealed this

Twenty-eighth Day of March, 1989

Attest:

DONALD J. QUIGG

Attesting Officer

Commissioner of Patents and Trademarks